(12) United States Patent
Takai

(10) Patent No.: US 8,839,944 B2
(45) Date of Patent: Sep. 23, 2014

(54) SAMPLE PROCESSING APPARATUS, SAMPLE TRANSPORTING DEVICE, AND SAMPLE RACK TRANSPORTING METHOD

(75) Inventor: Kei Takai, Kobe (JP)

(73) Assignee: Sysmex Corporation, Kobe-Shi, Hyogo (JP)

( * ) Notice: Subject to any disclaimer, the term of this patent is extended or adjusted under 35 U.S.C. 154(b) by 681 days.

(21) Appl. No.: 12/883,587

(22) Filed: Sep. 16, 2010

(65) Prior Publication Data

US 2011/0073438 A1    Mar. 31, 2011

(30) Foreign Application Priority Data

Sep. 25, 2009   (JP) ................................ 2009-221210

(51) Int. Cl.
| | |
|---|---|
| *B65G 47/10* | (2006.01) |
| *G01N 35/02* | (2006.01) |
| *G01N 35/04* | (2006.01) |

(52) U.S. Cl.
CPC ...... *G01N 35/026* (2013.01); *G01N 2035/0415* (2013.01); *G01N 2035/0465* (2013.01)
USPC ....................................... 198/367; 198/346.1

(58) Field of Classification Search
USPC ........... 198/339.1, 346.1, 346.2, 368, 370.07, 198/580, 597, 347.4, 348, 367, 370.08, 198/836.1, 836.4, 836.3, 463.4, 468.1, 198/468.11, 436, 437, 347.1, 456, 458, 198/459.6, 459.1, 465.1, 465.2, 345.1, 198/345.2, 345.3, 369.7
See application file for complete search history.

(56) References Cited

U.S. PATENT DOCUMENTS

| | | | | |
|---|---|---|---|---|
| 2,839,177 | A * | 6/1958 | Immesberger | ............. 198/463.4 |
| 4,325,476 | A * | 4/1982 | Eddy | ............................. 198/448 |
| 4,506,777 | A * | 3/1985 | Kampf | ..................... 198/341.02 |
| 5,133,446 | A * | 7/1992 | Draghetti | ................... 198/418.5 |
| 5,207,986 | A * | 5/1993 | Kadota et al. | ................... 422/65 |
| 5,380,488 | A * | 1/1995 | Wakatake | ........................ 422/65 |
| 5,876,670 | A * | 3/1999 | Mitsumaki et al. | ............. 422/65 |
| 5,972,295 | A * | 10/1999 | Hanawa et al. | ................. 422/65 |
| 5,985,215 | A * | 11/1999 | Sakazume et al. | .............. 422/67 |
| 6,061,899 | A * | 5/2000 | Cardini et al. | .................. 29/736 |
| 6,117,392 | A * | 9/2000 | Hanawa et al. | ................. 422/65 |
| 6,290,907 | B1 * | 9/2001 | Takahashi et al. | .............. 422/65 |
| 6,654,663 | B1 * | 11/2003 | Jokela | .......................... 700/230 |
| 6,827,902 | B1 * | 12/2004 | Kuriyama et al. | .............. 422/65 |

(Continued)

FOREIGN PATENT DOCUMENTS

| | | |
|---|---|---|
| JP | 2001-074754 A | 3/2001 |
| JP | 2001-153875 A | 6/2001 |

(Continued)

*Primary Examiner* — William R Harp
(74) *Attorney, Agent, or Firm* — Brinks Gilson & Lione

(57) ABSTRACT

A sample processing apparatus which has a transporting device; a sample processing device, the transporting device has a first transport path; a second transport path; a rack moving mechanism for moving the sample rack from the first transport path to the second transport path; a guide member, movable in vertical directions, for allowing the sample rack to move from the first transport path to the second transport path when the guide member is at a predetermined position, and for preventing the sample rack being transported on the first transport path or the second transport path from deviating from the transport path when the guide member is above the predetermined position; and a drive source for moving the guide member in vertical directions. Also, a sample transporting device, and a sample rack transporting method.

20 Claims, 14 Drawing Sheets

(56) References Cited

U.S. PATENT DOCUMENTS

| | | | |
|---|---|---|---|
| 6,924,152 B2 * | 8/2005 | Matsubara et al. | 436/180 |
| 7,028,831 B2 * | 4/2006 | Veiner | 198/619 |
| 7,264,111 B2 * | 9/2007 | Veiner | 198/619 |
| 7,300,628 B2 * | 11/2007 | Nogawa et al. | 422/65 |
| 7,331,474 B2 * | 2/2008 | Veiner et al. | 211/74 |
| 7,681,466 B2 * | 3/2010 | Miller et al. | 73/864.31 |
| 7,842,237 B1 * | 11/2010 | Shibuya et al. | 422/64 |
| 7,850,914 B2 * | 12/2010 | Veiner et al. | 422/65 |
| 7,854,892 B2 * | 12/2010 | Veiner et al. | 422/65 |
| 7,858,032 B2 * | 12/2010 | Le Comte et al. | 422/65 |
| 7,939,020 B2 * | 5/2011 | Nogawa et al. | 422/65 |
| 7,998,409 B2 * | 8/2011 | Veiner et al. | 422/65 |
| 8,252,233 B2 * | 8/2012 | Tokieda et al. | 422/65 |

FOREIGN PATENT DOCUMENTS

| | | |
|---|---|---|
| JP | 2002-249221 A | 9/2002 |
| JP | 2003-066050 A | 3/2003 |
| JP | 2007-223795 A | 9/2007 |

* cited by examiner

SAMPLE PROCESSING APPARATUS, SAMPLE TRANSPORTING DEVICE, AND SAMPLE RACK TRANSPORTING METHOD

RELATED APPLICATIONS

This application claims priority under 35 U.S.C. §119 to Japanese Patent Application No. 2009-221210 filed on Sep. 25, 2009, the entire content of which is hereby incorporated by reference.

BACKGROUND OF THE INVENTION

1. Field of the Invention

The present invention relates to a sample processing apparatus for transporting samples and processing the transported samples, sample transporting device, and sample rack transporting method.

2. Background of the Related Arts

Analyzer are known to be provided with a plurality of measuring units, and a transporting device for transporting sample racks to the plurality of measuring units, and the transporting device in such analyzers is provided with a plurality of transport paths. Such analyzers provided with a plurality of transport paths have mechanisms for moving sample racks during transport from one transport path to another transport path (for example, refer to Japanese Laid-Open Patent Publication No. 2001-074754).

The analyzer disclosed in Japanese Laid-Open Patent Publication No. 2001-074754 is provided with a first sample feed line, second sample feed line, and a sample return line, and the sample rack is moved between these transport paths by a line changer. The line changer has a change guide that is movable between transport paths. The change guide is provided with two plate members disposed so as to form an empty space therebetween for the insertion of a sample rack, such that the sliding sample rack, which is held between by two plate members, is moved between transport paths by the change guide moving between transport paths. In order to slide the sample rack in this manner, a guide for guiding the sample rack in the transport direction is not provided in the part of the first sample feed line, second sample feed line, and sample return line corresponding to the moving range of the line changer of the transporting device, and the sample rack mounting surface of these transport lines are stepless.

The transporting device disclosed in Japanese Laid-Open Patent Publication No. 2001-074754 has, in the transporting device, parts that are not provided with a guide for guiding the movement of the sample rack in the transport direction. There is therefore concern that the sample rack being transported on the transport line may deviate from the transport path.

SUMMARY OF THE INVENTION

The scope of the present invention is defined solely by the appended claims, and is not affected to any degree by the statements within this summary.

According to a first aspect of the present invention, a sample processing apparatus comprising: a transporting device for transporting a sample rack holding a sample; a sample processing device for processing the sample held by the sample rack transported by the transporting device, wherein the transporting device comprises: a first transport path for transporting the sample rack; a second transport path for transporting the sample rack, disposed parallel to the first transport path; a rack moving mechanism for moving the sample rack from the first transport path to the second transport path; a guide member, movable in vertical directions, for allowing the sample rack to move from the first transport path to the second transport path when the guide member is at a predetermined position, and for preventing the sample rack being transported on the first transport path or the second transport path from deviating from the transport path when the guide member is above the predetermined position; and a drive source for moving the guide member in vertical directions.

According to a second aspect of the present invention, a sample transporting device comprising: a first transport path for transporting the a sample rack holding a sample; a second transport path for transporting the sample rack, disposed parallel to the first transport path; a rack moving mechanism for moving the sample rack from the first transport path to the second transport path; a guide member, disposed to be movable in vertical directions between the first transport path and the second transport path, for allowing the sample rack to move from the first transport path to the second transport path when at a predetermined position, and for preventing the sample rack being transported on at least one of the first transport path and or the second transport path from deviating from the transport path when the guide member is above the predetermined position; and a drive source for moving the guide member in vertical directions.

According to a third aspect of the present invention, a sample processing apparatus comprising: a transporting device for transporting a sample rack holding a sample; a sample processing device for processing a sample held by the sample rack transported by the transporting device, wherein the transporting device comprises: a first transport path for transporting the sample rack; a second transport path for transporting the sample rack, disposed parallel to the first transport path; a rack moving mechanism for moving the sample rack from the first transport path to the second transport path; a guide member, movable in vertical directions, for guiding the sample rack being transported on the first transport path or second transport path when the guide member is at a predetermined position; a drive source for moving the guide member in vertical directions, wherein the guide member permits movement of the sample rack from the first transport path to the second transport path by the rack moving mechanism when the guide member is below the predetermined position.

According to a fourth aspect of the present invention, a method for transporting a sample rack by a transporting device comprising a first transport path for transporting the sample rack, a second transport path for transporting the sample rack and disposed parallel to the first transport path, and a rack moving mechanism for moving the sample rack from the first transport path to the second transport path, comprising the steps of: moving a guide member to a predetermined position to allow movement of the sample rack from the first transport path to the second transport path when the sample rack is to be moved from the first transport path to the second transport path; and moving the guide member above the predetermined position to prevent the sample rack from deviating from the transport path when the sample rack is being transport one of the first transport path or the second transport path.

DETAILED DESCRIPTION OF THE PREFERRED EMBODIMENTS

The preferred embodiment of the present invention is described hereinafter with reference to the drawings.

The present embodiment is a sample processing apparatus provided with a sample transporting device and a plurality of measuring units for measuring samples; wherein the sample transporting device incorporates a transport line (first transport path) for transporting a sample rack in one direction that does not pass through a sample supplying position for supplying a sample to a measuring unit, and a return line (second transport path), disposed parallel to the transport path, for transporting the sample rack in the reverse direction to the one direction that does not pass through the sample supplying position, and a transport line (third transport path) for transporting the sample rack to the sample supplying position, a guide member disposed between the transport path and the return path so as to be movable in vertical directions for permitting the movement of the sample rack from the transport line to the return line when the guide member is at a predetermined position and preventing deviation from the line by the sample rack being transported on the transport line and return line when the guide member has been moved above the standard position, and a motor for moving the guide member vertically.

[Structure of the Sample Processing Apparatus]

Figure 1:
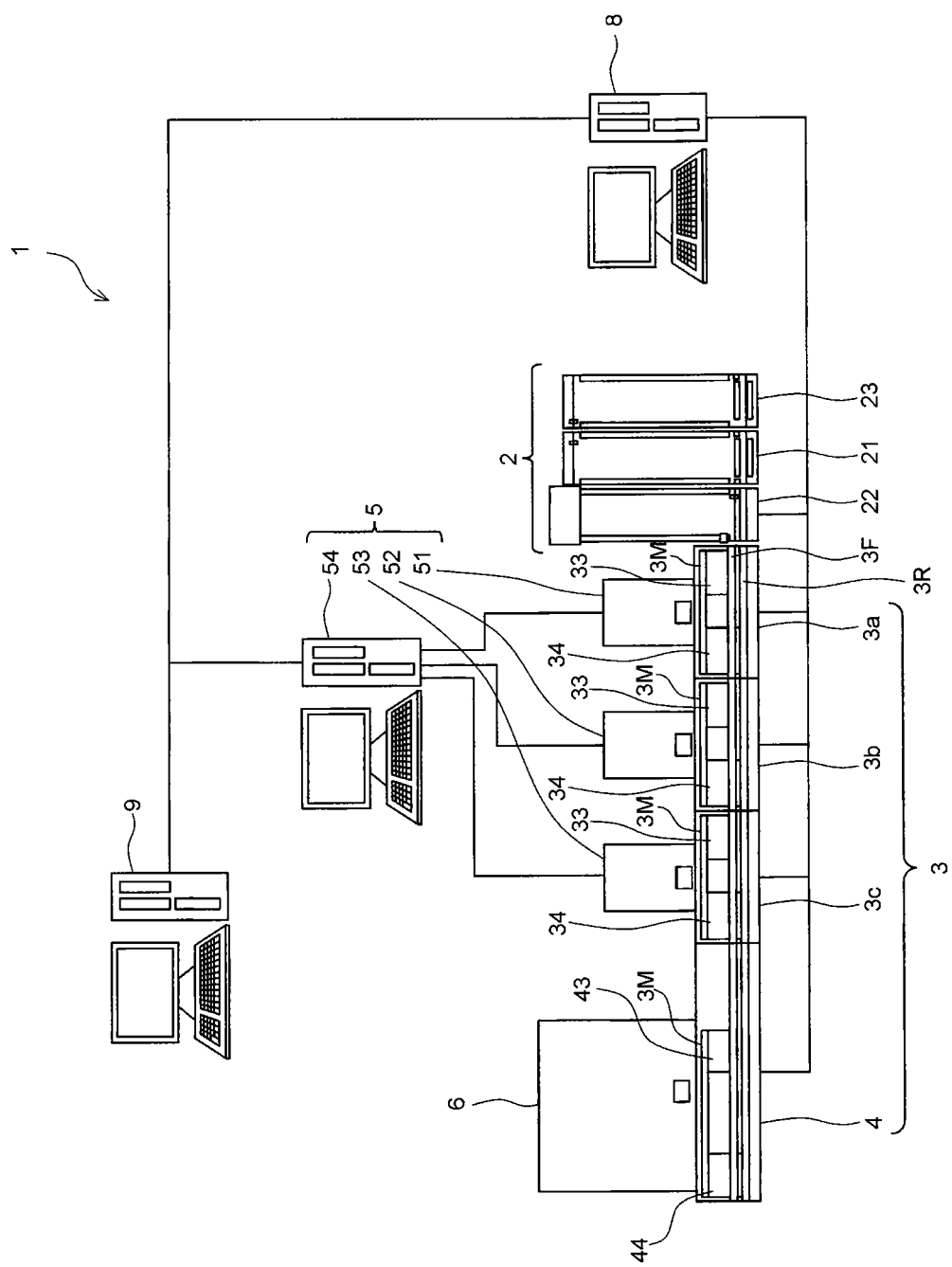
FIG. 1 is a brief plan view showing the general structure of an embodiment of the sample processing apparatus.

FIG. 1 is a brief plan view showing the general structure of an embodiment of the sample processing apparatus. As shown in FIG. 1, the sample processing apparatus 1 includes a sample collecting device 2, sample transporting device 3, blood cell analyzer 5, smear preparing apparatus 6, and system control device 8. The sample processing apparatus 1 of the present embodiment is connected to a sample information managing device 9 via a communication network so as to allow communication therebetween. The sample transporting device 3 has sample transporting units 3a, 3b, 3c, and 4, and the sample transporting units 3a, 3b, 3c, and 4 are mutually connected in series to extend in the horizontal direction in the drawing. The sample transporting device 3 has a transport line 3F for transporting a sample rack holding a plurality of samples in a leftward direction in the drawing, the line 3F being disposed linearly in the horizontal direction along the sample transport units 3a, 3b, 3c, and 4, and a return line 3R for transporting the sample rack in a rightward direction in the drawing, the line 3R being disposed parallel to the transport line 3F.

The blood analyzer 5 is provided with three measuring units 51, 52, and 53; the measuring unit 51 is disposed in back of the sample transporting unit 3a, the measuring unit 52 is disposed in back of the sample transporting unit 3b, and the measuring unit 53 is disposed in back of the sample transporting unit 3c. The smear preparing apparatus 6 is also disposed behind the sample transporting unit 4. The measurement lines 3M for transporting the sample rack L extend in a lateral direction before each of the sample transporting units 3a, 3b, 3c, and 4 to supply the sample to the measuring units 51, 52, 53 and smear preparing apparatus 6. A feed path for feeding the sample rack from the transport line 3F to the origin of the measurement line 3M is disposed between the transport line 3F and each measurement line 3M.

The sample collecting device 2 for receiving sample racks is provided with a sample receiving unit 21 for receiving a sample rack from an operator, a preprocessing unit 22 for reading sample barcodes from the sample containers held in the sample rack, and a sample collecting unit for collecting the sample rack holding the processed samples. The sample collecting device 2 is connected to the right end of the sample transporting device 3; after the preprocessing unit 22 has read the rack ID and sample ID, the sample rack received by the sample receiving unit 21 of the sample collecting device 2 transports the sample rack to the transport line 3F of the sample transporting device 3. The sample rack is transported from the transport line 3F to the measurement line 3M through the measuring unit 51, 52, 53, or the preanalysis holder 33 or preanalysis rack holder 43 in the sample transport unit 3a, 3b, 3c, or 4 corresponding to the smear preparing apparatus 6, then the sample rack is transported on the measurement line 3M to the transport destination of the measuring unit 51, 52, 53, or smear preparing apparatus 6. After the sample has been supplied to the measuring unit 51, 52, 53, or smear preparing apparatus 6, the sample rack L passes from the measurement line 3M through the preanalysis rack holder 34 or preprocessing holder 44 to the return line 3R, then in a rightward direction by the return line 3R to be collected by the sample collecting unit 23 of the sample collecting device 2. The structure of the sample processing device 1 is described in detail below.

Figure 2:
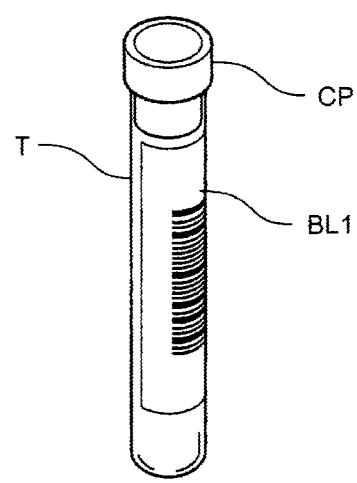
FIG. 2 is a perspective external view of a sample container.
Figure 3:
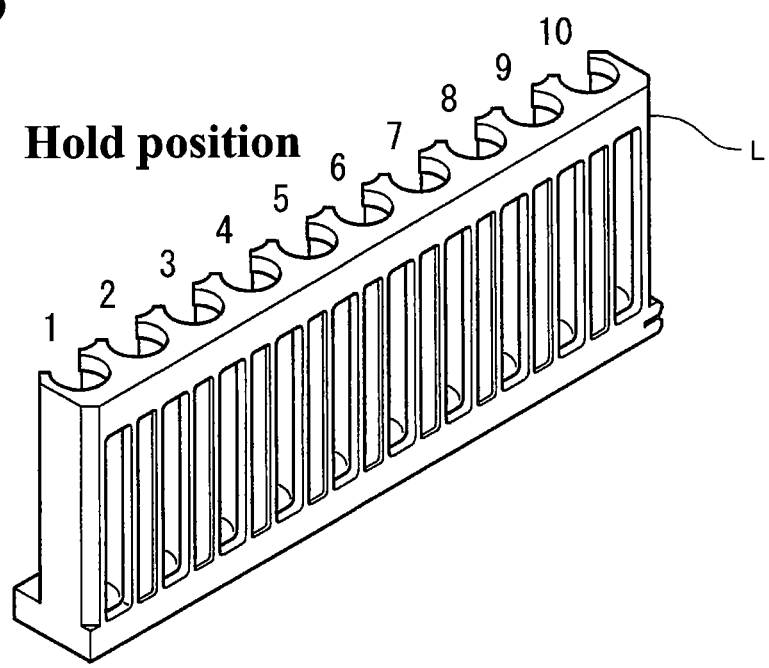
FIG. 3 is a perspective external view of a sample container.

FIG. 2 is an external perspective view of a sample container, and FIG. 3 is an external perspective view of a sample rack. As shown in FIG. 2, a sample container T has a tubular shape with an open top end. A blood sample collected from a patient is held within the container, and the opening at the top end is sealed by a cap CP. The sample container T is configured of transparent glass or synthetic resin, and the blood sample within is visible. A barcode label BL1 is also adhered to the side surface of the sample container T. A barcode (sample barcode) representing the sample ID is printed on the barcode label BL1. The sample rack L is capable of holding ten sample containers T in a row. Each sample container T is held in a vertical state (upright position) in the sample rack L. A barcode label (not shown in the drawing) is also adhered to the side surface of the sample container L on the measuring unit side between the holding position 1 and holding position 2. A barcode (rack barcode) indicating the rack ID is printed on this barcode label.

[Structure of the Sample Transporting Device 3]

The structure of the sample transporting device 3 is described below.

Figure 4:
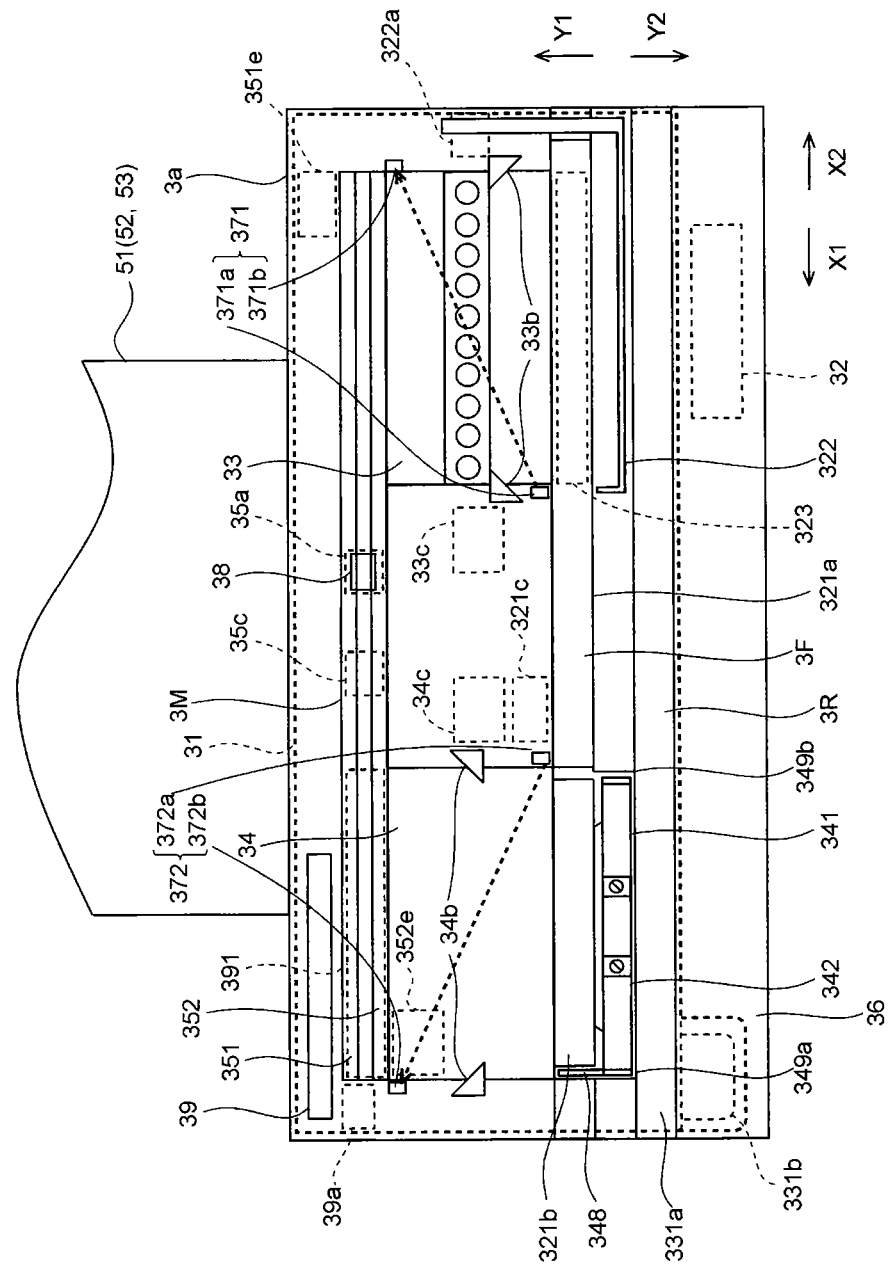
FIG. 4 is a plan view showing the structure of a sample transporting unit of the blood analyzer of the embodiment.

FIG. 4 is a plan view showing the structure of a sample transporting unit 3a. Although the description pertains to the sample transporting unit 3a installed on the front side of the measuring unit 51, the sample transporting units 3b and 3c installed on the front sides of the measuring units 52 and 53 have the same structures. As shown in FIG. 4, the sample transporting unit 3a is provided with a transport mechanism 31 for transporting a sample, and a controller 32 for controlling the transport mechanism 31. The transporting mechanism 31 is provided with a preanalysis rack holder 33 capable of temporarily holding a sample rack L that holds sample containers T containing as yet unanalyzed samples, post-analysis rack holder 34 capable of temporarily holding a sample rack L that holds sample containers T from which sample has been aspirated by the corresponding measuring unit 51, feed line 3F (first transport path) for receiving the sample rack L from the upstream device (sample collecting device 2) in the transport direction and delivering the sample rack L to the downstream device (sample transport unit 3b) in the transport direction without supplying the sample contained in the sample rack L to the measuring unit 51, return line 3R (second transport path) for receiving the sample rack L from the downstream device (sample transporting unit 3b) in the transport direction and delivering the sample rack L to the upstream device (sample collecting device 2) in the transport direction without supplying the sample contained in the sample rack L to the measuring unit 51, and measurement line 3M (third transport path) for moving the sample rack L horizontally in a straight line in the arrow X1 and X2 directions in the drawing to supply sample to the measuring unit 51 and transporting the sample rack L received from the preanalysis rack holder 33 to the post-analysis rack holder 34.

The feed line 3F extends in the arrow X1 direction in the drawing, and is capable of moving the sample rack L horizontally in a straight line in the arrow X1 direction (downstream side in the transport direction). The feed line 3F has two endless belts 321a and 321b disposed laterally, and a stepping motor 321c for driving the endless belts 321a and 321b.

The return line 3R is disposed parallel to the feed line 3F a predetermined distance in front of the feed line 3F. The return line 3R is capable of moving the sample rack L horizontally in a straight line in the arrow X2 direction (upstream side in the transport direction), which is the opposite of the X1 direction. The return line 3R has an endless belt 331a and stepping motor 331b, and is configured to rotate the belt 331a in the arrow X2 direction via the drive force of the stepping motor 331b. The sample rack L disposed on the belt 331a is thus moved in the arrow X2 direction.

A rack feeder 322 is disposed facing the preanalysis rack holder 33 on the front side of the preanalysis rack holder 33 with the feed line 3F medial thereto. The rack feeder 322 is configured to move horizontally in a straight line in the arrow Y1 direction (backward) via the drive force of a stepping motor 322a. Therefore, when the sample rack L is received by the feed line 3F from the device on the upstream side in the transport direction and the sample rack L arrives at the position 323 (hereinafter referred to as "preanalysis rack feeding position") on the feed line 3F between the preanalysis rack holder 33 and the rack feeder 322, the sample rack L is pushed into the preanalysis rack holder 33 by moving the rack feeder 322 to the preanalysis rack holder 33 side.

The preanalysis rack holder 33 has a square shape in planar view, and the length in the transverse direction is somewhat greater than the length of the sample rack L. The width (length in the front-to-back direction) of the preanalysis rack holder 33 is somewhat greater than twice the width of the sample rack L. The preanalysis rack holder 33 is a step lower from the peripheral surface, and the sample rack L is placed on this surface prior to analysis. The preanalysis rack holder 33 is capable of simultaneously holding two sample racks L. A rack sensor 371 is mounted in the vicinity of the preanalysis rack holder 33, so that the sample rack L held in the preanalysis rack holder 33 is detected by the rack sensor 371. The rack sensor 371 is an optical type sensor configured by a light emitting part 371a and a light receiving part 371b. Rack feeders 33b protrude toward the inner side from the bilateral side surfaces of the preanalysis rack holder 33. When a sample rack L is detected by the rack sensor 371, the rack feeders 33b engage the sample rack L and move the sample rack L backward by the rack feeders 33b moving backward (the direction approaching the measurement line 3M). The rack feeders 33b are driven by a stepping motor 33c disposed below the preanalysis rack holder 33.

As shown in FIG. 4, when the sample rack L has been moved from the preanalysis rack holder 33, the measurement line 3M moves the sample rack L in the X1 direction. A sample container detecting position 35a for detecting a sample container via the sample container sensor 38, and a sample supplying position 35c for supplying a sample to the measuring unit 51 of the blood cell analyzer 5 are provided on the transport path of the sample rack L on the measurement line 3M. The measurement line 3M is configured to transport the sample rack L through the sample container detecting position 35a so that the sample can be transported to the sample supplying position 35c. The sample supplying position 35c is a position two samples from the sample container detecting position 35a on the downstream side in the transport direction, that is, the position at which a sample is supplied to the measuring unit 51 by the hand part of the measuring unit 51 of the blood cell analyzer 5 gripping the sample container T containing the sample, taking the sample container T from the sample rack L and aspirating the sample from the sample container T when a sample has been transported to the sample supplying position 35c via the measurement line 3M. After the sample container T has been transported to the sample supplying position 35c and the sample supplying operation has ended, the measurement line 3M awaits the return of the sample container T to the sample rack L.

The measurement line 3M has a first belt 351 and second belt 352 that operate independently, and stepping motors 351e and 352e for respectively driving the two belts.

A rack feeder 39 is disposed facing the post-analysis rack holder 34 and medial to the measurement line 3M. The rack feeder 39 is configured to move horizontally in a straight line in the arrow Y2 direction via the drive force of a stepping motor 39a. Therefore, when the sample rack L has been transported to the position 391 (hereinafter referred to as "post-analysis rack feed position") between the post-analysis rack holder 34 and the rack feeder 39, the sample rack L is pushed into the post-analysis rack holder 34 by moving the rack feeder 39 to the post-analysis rack holder 34 side. Thus, after analysis, the sample rack L is fed from the measurement line 3M to the post-analysis rack holder 34.

The post-analysis rack holder 34 has a square shape in planar view, and the length in the transverse direction is somewhat greater than the length of the sample rack L. The width (length in the front-to-back direction) of the post-analysis rack holder 34 is somewhat greater than twice the width of the sample rack L. The post-analysis rack holder 34 is a step lower from the peripheral surface, and the sample rack L is placed on this surface after analysis. The post-analysis rack holder 34 is capable of simultaneously holding two sample racks L. A rack sensor 372 is mounted in the vicinity of the post-analysis rack holder 34, so that the sample rack L held in the post-analysis rack holder 34 is detected by the rack sensor 372. The rack sensor 372 is an optical type sensor configured by a light emitting part 372a and a light receiving part 372b. Rack receivers 34b protrude toward the inner side from the bilateral side surfaces of the post-analysis rack holder 34. When a sample rack L is detected by the rack sensor 372, the rack receivers 34b engage the sample rack L and move the sample rack L forward by the rack receivers 34b moving forward (the direction approaching the feed line 3F and return line 3R). The rack receivers 34b are driven by a stepping motor 34c disposed below the post-analysis rack holder 34. The post-analysis rack holder 34 is connected to the feed line 3F and return line 3R, so that the rack receivers 34b can move the sample rack L placed on the post-analysis rack holder 34 to the feed line 3F and return line 3R.

Figure 5:
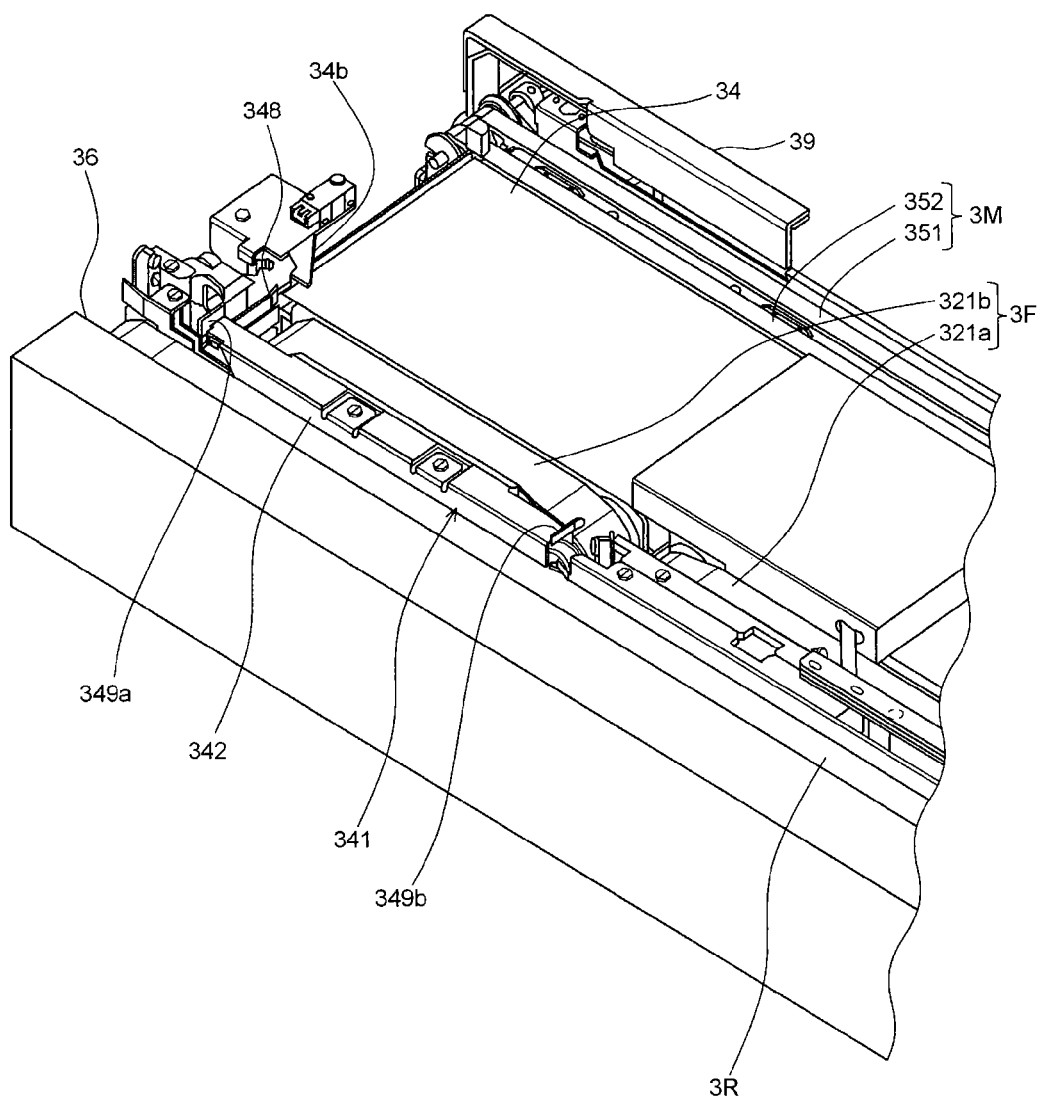
FIG. 5 is a partial enlargement showing the structure of part of the sample transporting unit of the embodiment.

FIG. 5 is an enlarged partial perspective view showing part of the structure of the sample transporting unit 3a. A guide mechanism 341 is provided at a position in front of the post-analysis rack holder 34 between the feed line 3F and return line 3R. The guide mechanism 341 is square in shape in planar view, and the width is slightly less than the distance between the feed line 3F and return line 3R. A wall 36 is disposed in front of and facing the guide mechanism 341 with the return line 3R therebetween. The wall 36 extends along the entire length of the return line 3R, and protrudes above the transport surface of the return line 3R. When the sample rack L is transported by the return line 3R, the sample rack L is therefore prevented from deviating from the return line 3R by the wall 36.

Figure 6:
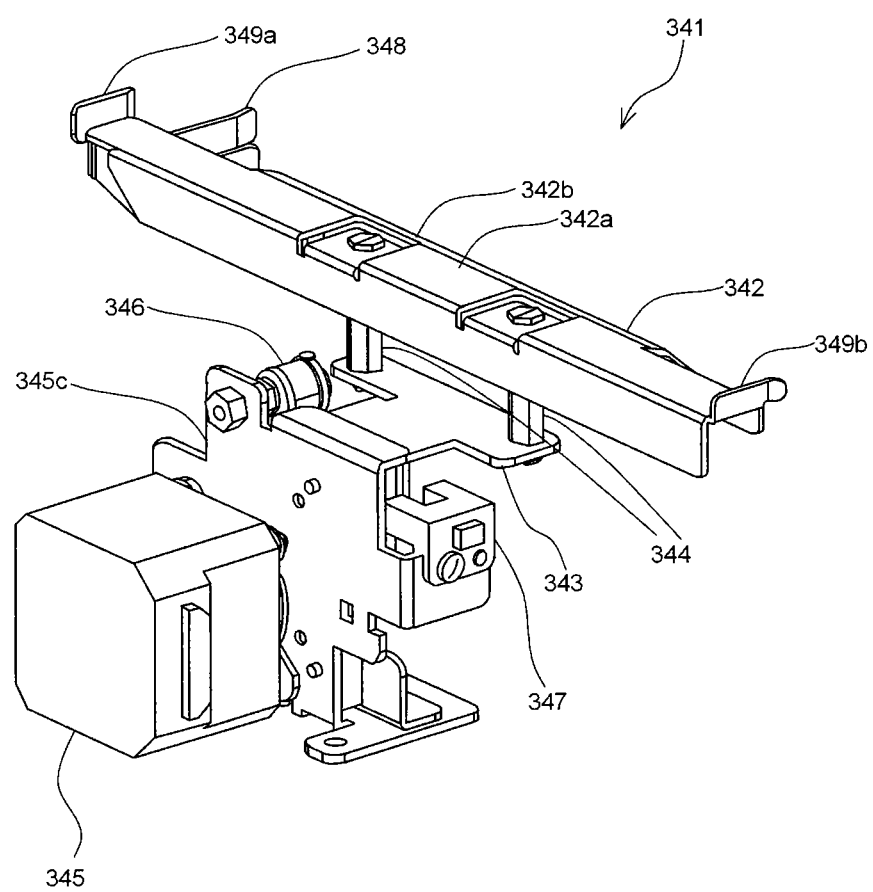
FIG. 6 is a perspective view showing the structure of the front side of the guide mechanism of the sample transporting unit.
Figure 7:
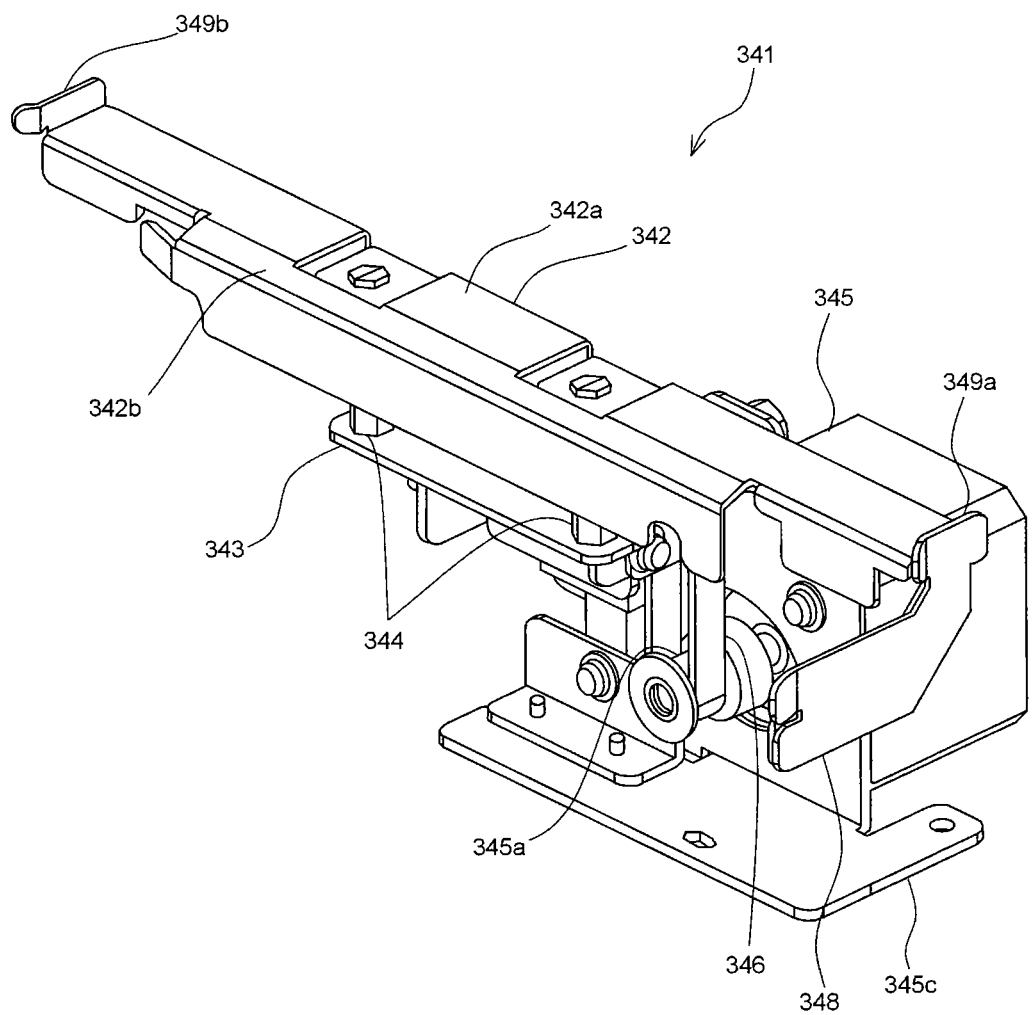
FIG. 7 is a perspective view showing the structure of the back side of the guide mechanism of the sample transporting unit.

FIG. 6 is a perspective view showing the structure of the front side surface of the guide mechanism 341, and FIG. 7 is a perspective view showing the structure of the back side surface of the guide mechanism 341. The guide mechanism 341 has a guide member 342 formed by a curved metal plate, and a support member 343 that supports the guide member 342 from below. Two rod-like connector members 344 are connected between the guide member 342 and the support member 343. A stepping motor 345 is also provided to drive the guide member 342, and a belt 346 is mounted to the output shaft of the stepping motor 345 through a pulley 345a. A pulley (not shown in the drawing) corresponding to the pulley 345a is also provided, so as to be freely rotatable, above the output shaft of the stepping motor 345. The support member 343 is fixed to one part of the belt 346. Through this configuration, the belt 346 is rotated between the pulleys separated in a vertical direction via the operation of the stepping motor 345 so that the support member 343 can move in vertical directions in correspondence therewith. As a result, the guide member 342 moves in the vertical directions.

A flat surface 342a is formed at the top end of the guide member 342, and an incline 342b is provided on the feed line 3F side (back side) of the flat surface 342a to connect thereto. The incline 342b decreases as it approaches the feed line 3F, and has a predetermined angle of inclination relative to the flat surface 342a.

A detection piece that is not shown in the drawing is mounted on the support member 343, and an optical type sensor 347 for detecting this detection piece is fixedly attached to a base member 345c on which the stepping motor 345 is mounted. The detection piece is detected by the optical type sensor 347 when the detection piece is moved in a vertical direction by the vertical movement of the support member 343 and arrives at the detection position of the optical type sensor 347. When the detection piece has been detected by the optical type sensor 347, the position of the guide member 342 is specified since the guide member 342 is at a specific position.

A movement stopper 348 is also fixedly attached to the end of the guide member 342 on the downstream side in the transport direction to stop the sample rack L being transported by the feed line 3F. The transport stopper 348 has a guide part 349a that protrudes upward from the end (end on the downstream side in the transport direction) toward the guide member 342. The other end (end on the upstream side in the transport direction) of the guide member 342 is bent upward at a right angle, and this part is the guide part 349b. The movement of the sample rack L is guided by the guide parts 349a and 349b when the sample rack L is moved from the feed line 3F to the return line 3R.

Figure 8A:
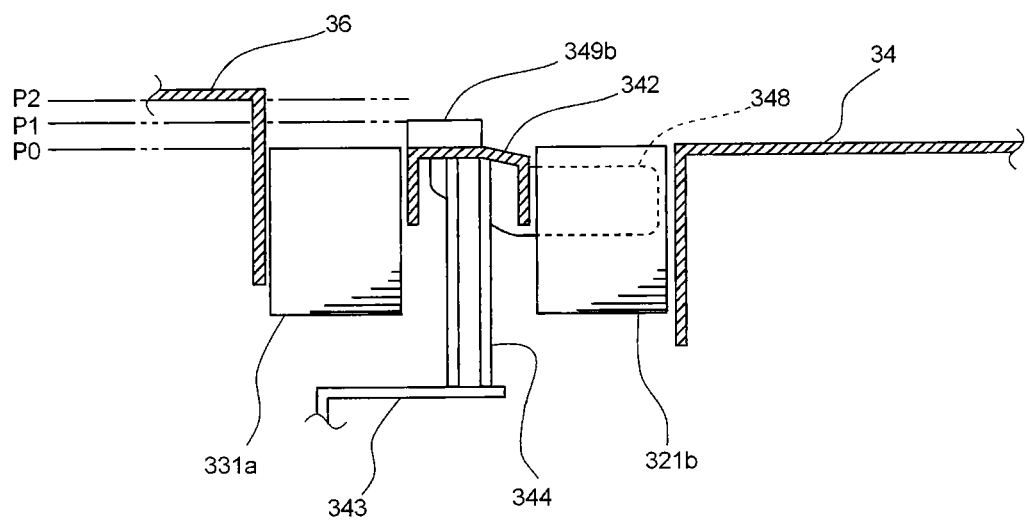
FIG. 8A is a cross sectional view illustrating the standard position of the guide member.
Figure 8B:
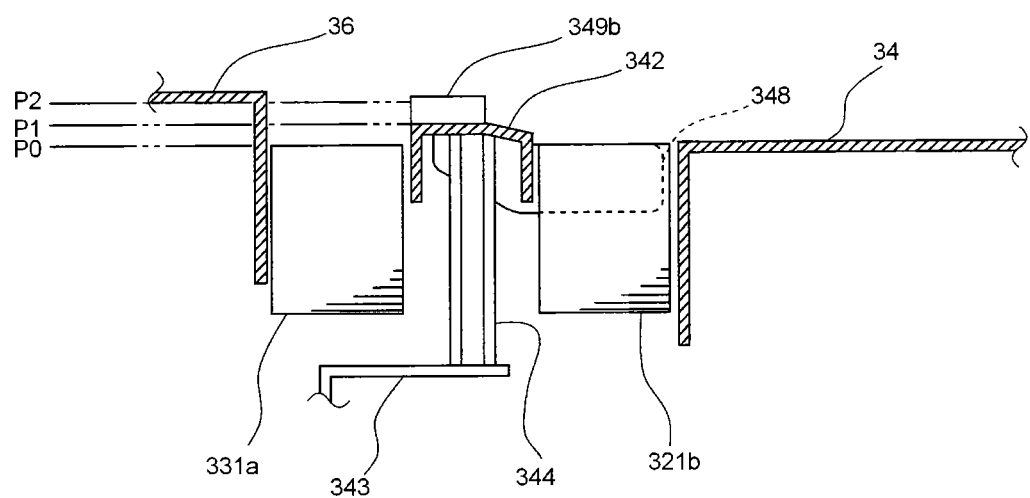
FIG. 8B is a cross sectional view illustrating the first extended position of the guide member.
Figure 8C:
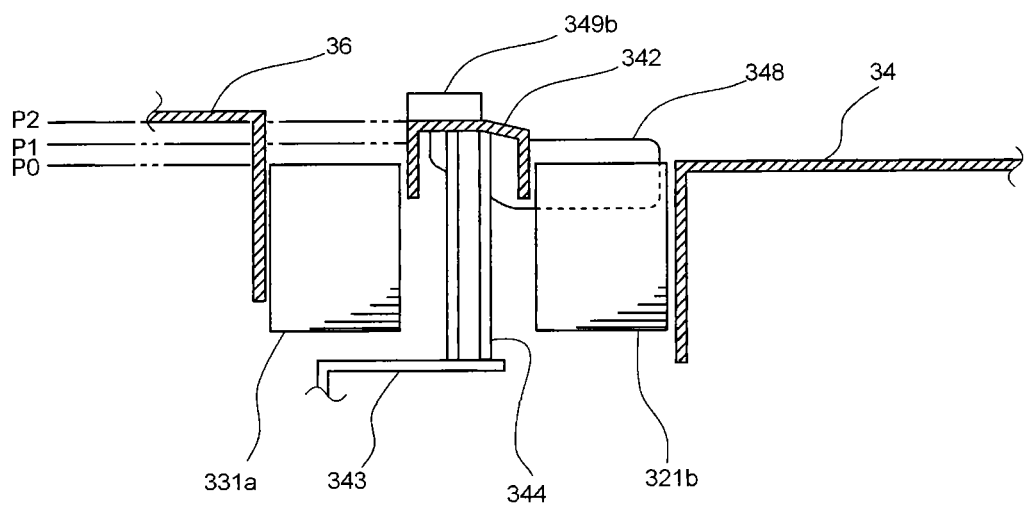
FIG. 8C is a cross sectional view illustrating the second extended position of the guide member.

FIGS. 8A, 8B, and 8C are cross sectional views illustrating the position of the guide member 342. FIG. 8A shows the standard position P0 of the guide member 342. The standard position P0 is the position at which the height of the flat surface 342a of the guide member 342 is substantially the same as the top surface of the respective feed line 3F and return line 3R. When the guide member 342 is at the standard position P0, the sample rack L is transported from the post-analysis rack holder 34, through the feed line 3F and guide member 342, to the return line 3R. The rack feeder 33b is capable of moving from the post-analysis rack holder 34 to the return line 3R (refer to FIG. 5); when the sample rack L held in the post-analysis rack holder 34 is collected in the sample collecting device 2 via the return line 3R, the sample rack L slides on the top surface of the post-analysis rack holder 34, feed line 3F, and guide member 342 to the return line 3R by positioning the guide member 342 so that the flat surface 342a is disposed at the standard position P0 and the rack feeder 33b is moved forward. At this time, the movement of the sample rack L is guided by the guide parts 349a and 349b as the sample rack L passes therebetween. When the flat surface 342a is disposed at the standard position P0, the tip of the incline 342b is lower than the top surface of the belt 321b of the feed line 3F; therefore, when the sample rack L moves from the feed line 3F to the guide member 342, the sample rack L is transported smoothly without catching on the corners or the like of the guide member 342, which would impede transport.

The guide member 342 moves upward from the standard position P0 so that the flat surface 342a is positioned at a first protruding position P1 above the standard position P0. FIG. 8B shows the first protruding position P1 of the guide member 342. When the guide member 342 is at the first protruding position P1, the guide member 342 protrudes from the respective top surfaces of the feed line 3F and return line 3R. When the sample rack L held on the post-analysis rack holder 34 is transported to the later stage devices by the feed line 3F, the sample rack L held in the post-analysis rack holder 34 is moved to the feed line 3F by positioning the guide member 342 at the first protruding position P1 and moving the rack feeder 34b forward. Since the guide member 342 protrudes above the top surface of the feed line 3F, the sample rack L does not go beyond the guide member 342 to the return line 3R. At this time the transport stopper 348 is positioned lower than the top surface of the feed line 3F, and the transport stopper 348 prevents the transport of the sample rack L by the feed line 3F. Further, since the guide member 342 protrudes above the top surface of the feed line 3F, the sample rack L is prevented from deviating from the feed line 3F by the guide member 342 when the sample rack L is transported by the feed line 3F.

The guide member 342 is then moved upward from the first protruding position P1, and disposed so that the flat surface 342a is positioned at a second protruding position P2 above the first protruding position P1. FIG. 8C shows the second protruding position P2 of the guide member 342. When the guide member 342 is at the second protruding position P2, the guide member 342 protrudes from the respective top surfaces of the feed line 3F and return line 3R, and the transport stopper 348 is positioned higher than the top surface of the feed line 3F. Therefore, movement of the sample rack L is prevented by the transport stopper 348 even when the sample rack L is transported by the feed line 3F so that the sample rack L is moved to the downstream side in the transport direction by the transport stopper 348.

The transporting mechanism 31 having the structure described above is mainly controlled by a controller 32. The controller 32 is configured by a CPU, ROM, RAM and the like, and a control program stored in the internal ROM of the transporting mechanism 31 can be executed by the CPU. The controller 32 has an ETHERNET™ interface that allows communications via a LAN with an information processing unit 54 and system control device 8.

As shown in FIG. 1, the sample transporting unit 4 is disposed on the front side of the smear sample preparing device 6. The right side end of the sample transporting unit 4 is connected to the sample transporting unit 3c positioned on the farthest downstream side in the direction of transport (left side in the drawing) among the three sample transporting units 3a, 3b, 3c.

Figure 9:
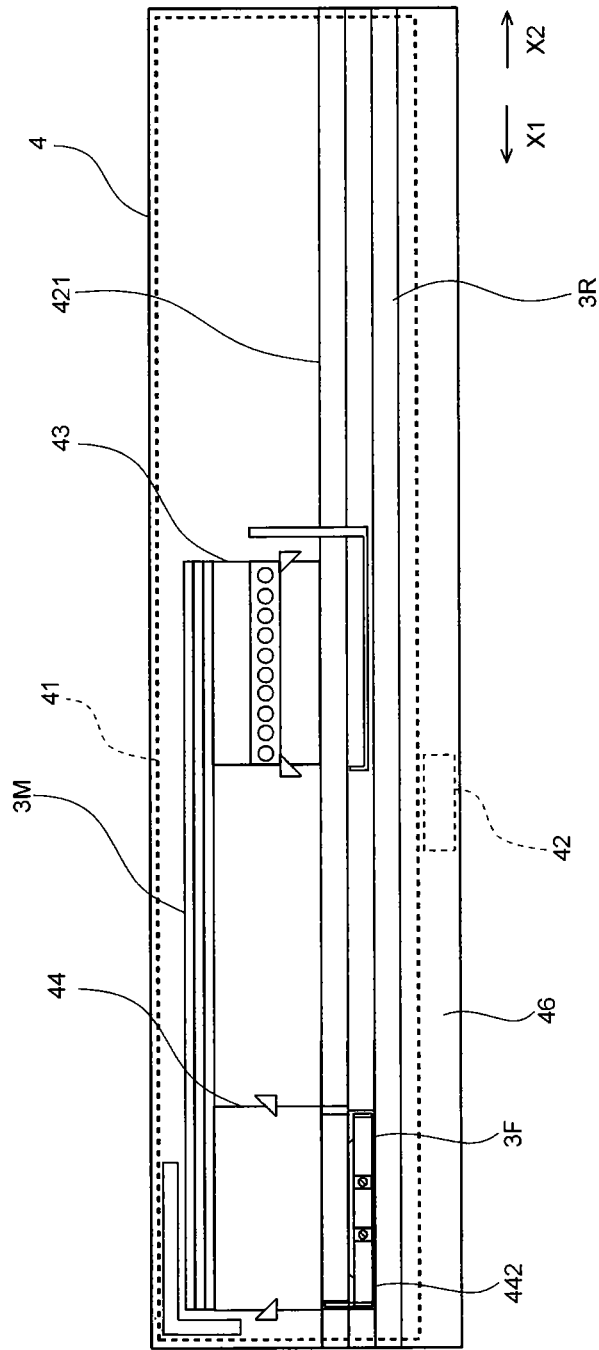
FIG. 9 is a plan view showing the structure of a sample transporting unit of the smear preparing apparatus of the embodiment.

FIG. 9 is a plan view showing the structure of the sample transporting unit 4. The sample transporting unit 4 is provided with a transport mechanism 41 for transporting a sample, and a controller 42 for controlling the transport mechanism 41. The transporting mechanism 41 is provided with a preprocessing rack holder 43 capable of temporarily holding a sample rack L that holds sample containers T containing as yet unprepared smear samples, post-processing rack holder 44 capable of temporarily holding the sample rack L that holds sample containers T from which sample has been aspirated by the smear sample preparing device 6, feed line 3F (first transport path) for receiving the sample rack L from the sample transporting unit 3c on the upstream side in the transport direction and transporting the sample rack L in the X1 direction, return line 3R (second transport path) for sending the sample rack L after smear sample processing to the sample collecting device 2 and moving the sample rack L to the sample transporting unit 3c on the upstream side in the transport direction, and a measurement line 3M (third transport path) for supplying the sample to the smear sample preparing device 6, moving the sample rack L horizontally in the X1 direction and moving the sample rack L received from the preprocessing rack holder 43 to the post-processing rack holder 44. A guide mechanism 441 that has a guide member 442 is disposed between the feed line 3F and return line 3R at a position in front of the post-processing rack holder 44. A wall 46 is disposed in front of and facing the guide mechanism 441 with the return line 3R therebetween. Note that although the size of structural components, shape, and positions of the transporting units 3a, 3b, and 3c differ, sample transporting device 4 components have the same functions and further description of their structures are abbreviated.

[Structure of the Blood Cell Analyzer 5]

The blood cell analyzer 5 is a multi-item blood cell analyzer using optical type flow cytometry to obtain the side scattered light intensity and fluorescent light intensity related to blood cells contained in a blood sample, classify the blood cells contained in the sample based on these data, count the number of blood cells of each type, prepare a scattergram color-coded for each cell type classified in this manner, and display the results. The blood cell analyzer 5 is provided with measuring units 51, 52, 53 for measuring blood samples, and an information processing unit 54 for processing the output from the measuring units 51, 52, 53, and displaying the blood sample analysis results.

Figure 10:
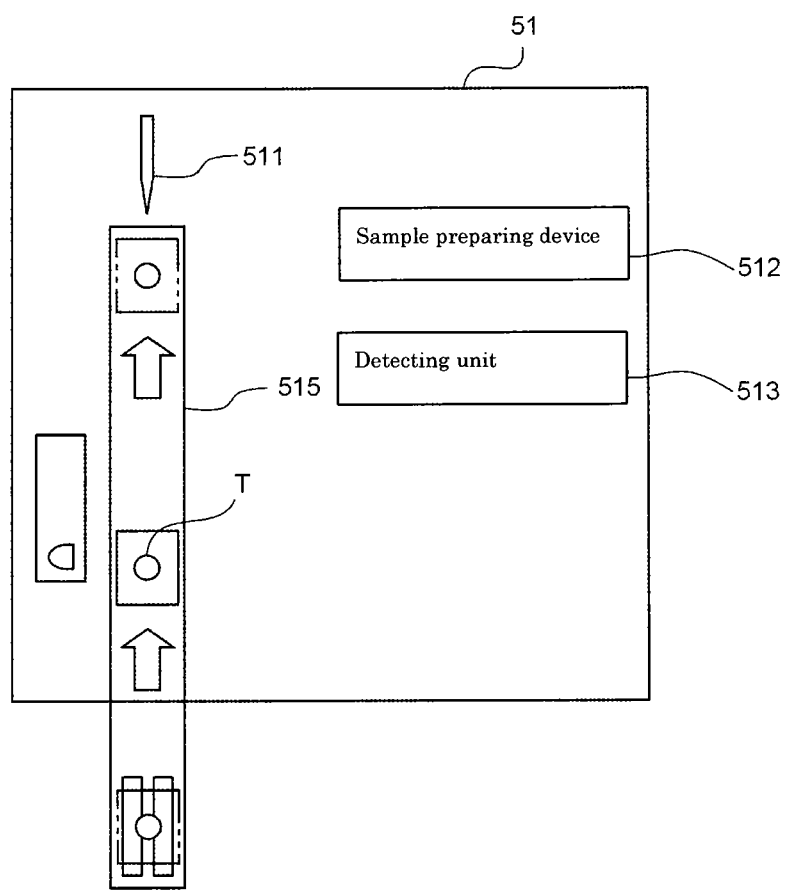
FIG. 10 is a block diagram showing the structure of the measuring unit provided in the blood analyzer of the embodiment.

FIG. 10 is a block diagram showing the structure of the measuring unit 51. As shown in FIG. 10, the measuring unit 51 has a sample aspirator 511 for aspirating the blood sample from the sample container (blood collection tube) T, sample preparing unit 512 for preparing a measurement sample from the blood aspirated by the blood aspirator 511, and a detector 513 for detecting blood cells from the measurement sample prepared by the sample preparing unit 512. The measuring unit 51 also has an inlet (not shown) for receiving, into the measuring unit 51, a sample container T held in the sample rack L transported by the measurement line 3M of the sample transporting unit 3a, and a sample container feeder 515 for receiving the sample container T from the sample rack L into the measuring unit 51 and transporting the sample container T to the aspirating position of the sample aspirator 511.

An aspirating tube (not shown) is provided on the tip of the sample aspirator 511. The sample aspirator 511 is movable in vertical directions; the sample aspirator 511 is configured to move downward to pierce the cap CP of the sample container T that has been transported to the aspirating position, and aspirate the blood within the container.

The sample preparing unit 512 is provided with a plurality of reaction chambers (not shown). The sample preparing unit 512 is connected to reagent containers that are not shown in the drawing; these reagent containers supply reagents such as staining reagent, hemolytic agent, and diluting liquid to the reaction chambers. The sample preparing unit 512 is also connected to the aspirating tube of the sample aspirator 511, and supplies the blood sample aspirated by the aspirating tube to the reaction chambers. The sample preparing unit 512 prepares the sample (measurement sample) to be used for measurement by the detection unit 513 by mixing the sample and reagent within the reaction chamber.

The detection unit 513 uses a sheath flow DC method for RBC (red blood cell) detection, and PLT (platelet) detection. In the RBC and PLT detection using the sheath flow DC method, a sample and diluting liquid are mixed to form a measurement sample that is measured, and the total numbers of RBC and PLT are counted by the information processing unit 54 analyzing the measurement data obtained in this manner. The detection unit 513 uses an SLS-hemoglobin method to detect HGB (hemoglobin), and is configured to perform WBC (white blood cell) detection by flow cytometry using a semiconductor laser. In the detection unit 513, a measurement sample is prepared by mixing a sample, hemolytic agent, and diluting liquid, and the information processing unit 54 analyzes the measurement data obtained in this way to obtain the number of WBC and classify the WBC into five types.

The measuring units 52 and 53 have structures identical to that of the measuring unit 51, and are provided with a sample aspirator, sample preparing unit, detecting unit, and sample container transporter.

[Structure of the Smear Sample Preparing Device 6]

The smear sample preparing device 6 aspirates a blood sample, drips a droplet of the sample onto a slide glass, smears the droplet of the blood sample into a thin film on the slide glass which is then dried, after which a staining agent is applied to the slide glass to stain the blood on the slide glass and complete preparation of the smear sample.

Figure 11:
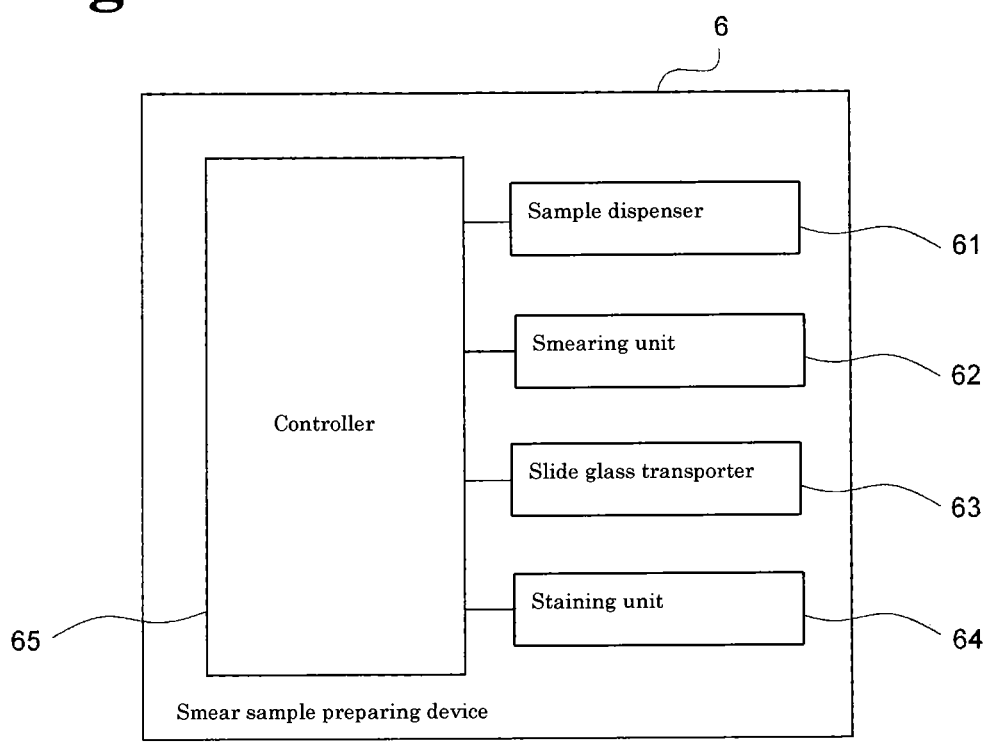
FIG. 11 is a block diagram briefly showing the structure of an embodiment of the smear preparing apparatus.

FIG. 11 is a block diagram briefly showing the structure of the smear sample preparing device 6. As shown in FIG. 11, the smear sample preparing device 6 is provided with a sample dispenser 61, smearing unit 62, slide glass transporter 63, staining unit 64, and controller 65.

The sample dispenser 61 is provided with an aspirating tube (not shown); the aspirating tube pierces the cap CP of the sample container T in the sample rack L transported on the measurement line 3M of the sample transporting unit 4, and aspirates the blood sample from the sample container T. The sample dispenser 61 is configured to drip the aspirated sample onto the slide glass. The smearing unit 62 smears the blood sample that has been dripped onto the slide glass, which is then dried and printed on the slide glass.

The slide glass transporter 63 houses the slide glasses on which a blood sample has been smeared by the smearing unit 62 in a cassette that is not shown in the drawing, and transports the cassette. The staining unit 64 supplies staining liquid to the slide glass inside the cassette that has been transported to a staining position by the slide glass transporter 63. The controller 65 executes control of the sample dispenser 61, smearing unit 62, slide glass transporter 63, and staining unit 64 to perform the smear sample preparation process described above according to the sample preparation instructions received from the sample transporting device 3.

[Operation of the Sample Processing Device]

The operation of the sample processing device 1 of the present embodiment is described below.

The sample processing device 1 receives an instruction to start sample processing when the sample processing device 1 starts the sample process. In this condition, when the sample rack L is received by the sample receiving unit 21, the sample rack L is transported to the preprocessing unit 22. The preprocessing unit 22 reads the rack ID of the sample rack L and the sample ID of each sample container T held in the sample rack L. The sample collecting device 2 sends the read rack ID, hold position, sample ID to the system control device 8. After receiving the rack ID, hold position, and sample ID, the system control device 8 queries the inspection information management device 9 for a measurement order, and stores the measurement order associated with the rack ID, hold position, and sample ID. The system control device 8 updates the sample rack L transport destination in real time in accordance with the stored measurement order and the operating conditions of the measurement units 51, 52, and 53. The sample rack L is then transported from the preprocessing unit 22 to the sample transporting unit 3a.

If the transport destination of the sample rack L is the measuring unit 51 corresponding to the sample transporting unit 3a, the sample transporting unit 3a that has received the sample rack L moves the sample rack L from the feed line 3F to the preanalysis rack holder 33. On the other hand, when the transport destination is the smear sample preparing device 6 or the measuring unit 52 or 53 corresponding to the sample transporting unit 3b, 3c, or 4 on the downstream side in the transport direction, the guide member 342 is moved to the position P1 and then the sample rack L is transported by the feed line 3F to directly deliver the sample rack L to the later stage sample transporting unit 3b.

After the sample rack L has been transported to the preanalysis rack holder 33, the sample rack L is moved from the preanalysis rack holder 33 to the measurement line 3M. The sample rack L is then moved to the sample supplying position 35c by the measurement line 3M, and the sample container T held in the sample rack L is measured by the measuring unit 51. When the measurement of all samples held in the sample rack L is completed, the sample rack L is moved to the post-analysis rack feed position 391 by the measurement line 3M, and then moved to the post-analysis rack holder 34 by the rack feeder 39.

Figure 12:
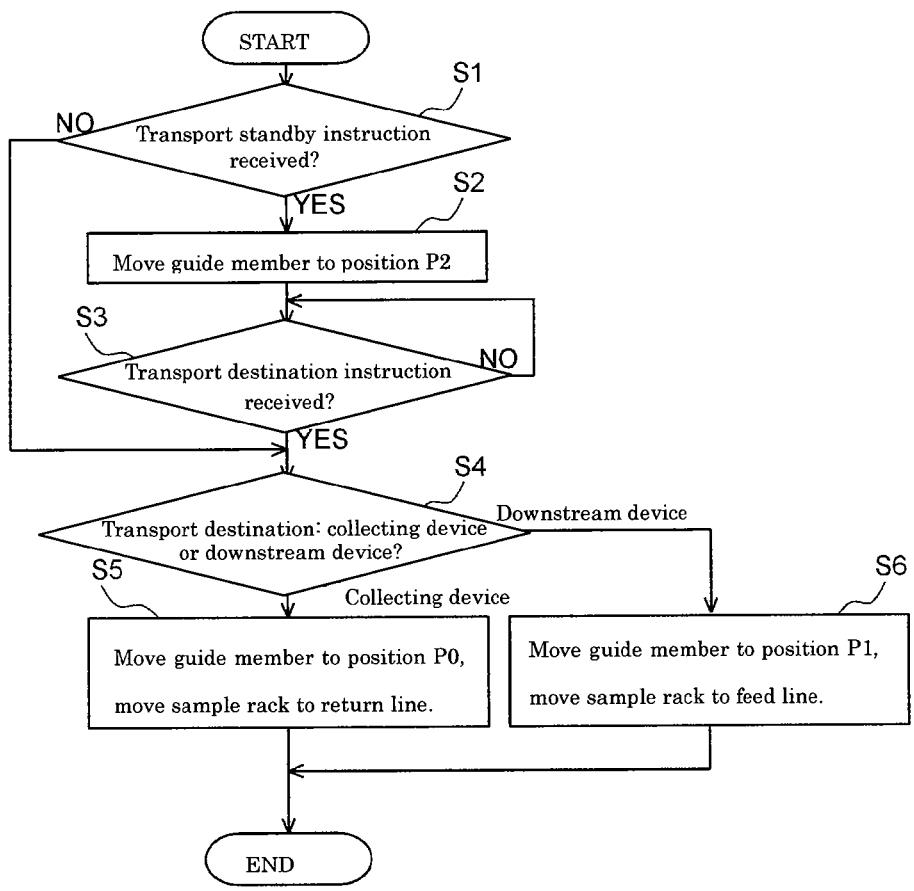
FIG. 12 is a flow chart showing the flow of the rack transporting operation of the sample transporting unit of the embodiment.

The operation of the sample transporting unit 3a after the sample rack L has been moved to the post-analysis rack holder 34 is described below based on the drawings. FIG. 12 is a flow chart showing the flow of the rack transporting operation of the sample transporting unit 3a of the present embodiment. The system control device 8 communicates with the sample transporting units 3a, 3b, 3c, and 4, and updates the sample rack transport condition in real time. When the transport destination of the sample rack L held in the post-analysis rack holder 34 has not been determined, for example, when the measurement result has not yet been obtained by the measuring unit 51 and re-examination by the measuring unit 51 is required to obtain a result, the system control device 8 sends data representing standby instructions (standby instruction data) to the sample transporting units 3a, 3b, 3c, and 4. On the other hand, when the transport destination of the sample rack L has been determined, the system control device 8 sends data representing the transport destination instruction (transport destination instruction data) to the sample transport units 3a, 3b, 3c, and 4. When the controller 32 of the sample transporting unit 3a (3b, 3c, 4) receives the standby instruction data or transport destination instruction data from the system control device 8, the process shown in FIG. 12 begins.

The controller 32 of the sample transporting unit 3a determines whether a destination standby instruction has been received from the system control device 8 based on the received data (step S1). When the received data are standby instruction data, that is, when a transport standby instruction for the sample rack L has been received from the system control device 8 (step S1: YES), the controller 32 moves the guide member 342 to position P2 (step S2). Thereafter, the controller 32 determines whether a transport destination instruction has been received (step S3). When a transport destination instruction has not been received, that is, when transport destination data have not been send from the system control device 8 (step S3: NO), the controller 32 repeats the process of step S3 until a transport destination instruction is received.

When the received data are not standby instruction data in step S1, that is, when the received data are transport instruction data (step S1: NO) or when a transport instruction has been received from the system control device 8 in step S3 (step S3: YES), the controller 32 determines whether the transport destination is the sample collecting unit 23 or a device on the downstream side in the transport direction (step S4). When the transport destination is the sample collecting unit 23 ('collecting unit' in step S4), the transport mechanism 31 is controlled to move the guide member 342 to the position P0; after the sample rack L has been moved from the post-analysis rack holder 34 to the return line 3R, the guide member 342 is moved to position P1 and the sample rack L is then moved from the return line 3R to the upstream side (X2 direction) (step S5), whereupon the process ends. At this time, the sample rack L slides on the top surfaces of the post-analysis rack holder 34, feed line 3F, and guide member 342, and is moved from the post-analysis rack holder 34 to the return line 3R. When the sample rack L moves from the feed line 3F to the return line 3R, the movement of the sample rack L is guided by passing between the guide members 349a and 349b. The sample rack L, which has been moved to the return line 3R, is held between the wall 36 and the guide member 342 at the position P1 and therefore prevented from deviating from the return line 3R by moving the guide member 342 to the position P1 after the sample rack L has moved to the return line 3R.

On the other hand, when the transport destination is a device on the downstream side in the transport direction in step S4 ('downstream device' in step S4), the controller 32 controls the actuation of the transport mechanism 31 to move the guide member 342 to position P1, then moves the sample rack L from the post-analysis rack holder 34 to the feed line 3F, and moves the sample rack L to the downstream side (X1 direction) via the feed line 3F (step S6), whereupon the process ends. The sample rack L, which has been moved to the feed line 3F, is supported on one side by the guide member 342 at the P1 position, and thus the sample rack L is prevented from deviating from the feed line 3F by the guide member 342 that has been moved to the P1 position.

According to the preferred configuration, when the guide members 342 and 442 are moved upward from the standard position P0 to the first protruding position P1, the sample rack L is prevented from deviating from the feed line 3F and return line 3R when being transported by the feed line 3F and return line 3R. When the guide members 342 and 442 are at the standard position P0, the sample rack L can be moved from the feed line 3F to the return line 3R so that the sample rack L can be efficiently recovered by the sample collecting device 2.

Since the height of the top surface of the guide member 342 is substantially the same as the height of the top surface of the feed line 3F and return line 3R when the guide member 342 is set at the standard position P0, the sample rack L can slide smoothly on the top surfaces of the feed line 3F, guide member 342, and return line 3R. Thus, the sample rack L can be moved from the post-analysis rack holder 34 to the return line 3R without requiring a complex mechanism if the rack feed 34b is provided to push the sample rack L from the post-analysis rack holder 34 to the return line 3R.

The guides 349a and 349b are provided at each end of the guide member 342; since the sample rack L passes between the guides 349a and 349b when the sample rack L is moved from the post-analysis rack holder 34 to the return line 3R, the movement of the sample rack L is guided by the guides 349a and 349b so as to prevent movement deviation such as the sample rack L becoming caught on the transport path.

When the sample rack L has not completed preparation for transport on the feed line 3F or when the such transport is unnecessary, the provision of the transport stopper 348 on the guide member 342 reliably prevents the movement of the sample rack L on the feed line 3F so that the sample rack L is not transported to the downstream side in the transport direction from the transport stopper 348.

Other Embodiments

Note that although the guide members 342 and 442 are configured to be movable among three positions including the standard position P0, first protruding position P1, and second protruding position P2 in the above embodiment, the present invention is not limited to this configuration. A configuration is also possible that provides a standard position P0 to move the sample rack L from the post-analysis rack holders 34 and 44 to the return line 3R, and a first protruding position P1 capable of moving between two positions when moving the sample rack L in the 1 direction via the feed line 3F.

Although the above embodiment has been described in terms of mounting a transport stopper 348 on the guide member 342 and integratedly moving the guide member 342 and transport stopper 348, the present invention is not limited to this configuration. A transport stopper may be provided separately from the guide member so that the guide member and the transport stopper move independently. In this case, the guide member is movable between two positions as mentioned above so that when the guide member is set at the position (first protruding position P1) at which it protrudes from the top surfaces of the feed line 3F and return line 3R, the transport stopper is retracted above the return line 3R in accordance with the transport condition of the other sample racks L on the feed line 3F; and the guide member can move among the same three positions as in the above embodiment so that the transport stopper protrudes above the top surface of the feed line 3F when the transport stopper is moved in linkage with the movement of the guide member that is disposed at the second protruding position P2, and the transport stopper is positioned below the top surface of the feed line 3F when the guide member is set at the standard position P0 or the first protruding position P1.

Although the sample rack L is prevented from deviating from both the feed line 3F and the return line 3R during transport by the guide member 342 in the above embodiment, the present invention is not limited to this configuration. The sample rack L may also be prevented from deviating only during transport on the feed line 3F, or the sample rack L may be prevented from deviating only during transport on the return line 3R by the guide member 342. Furthermore, a guide member for preventing deviation of the sample rack L only during transport on the feed line 3F, and a guide member for preventing deviation of the sample rack L only during transport on the return line 3R may be provided separately.

Although the above embodiment has been described in terms of providing the guide member 342 between the feed line 3F and return line 3R so that the sample rack L is moved from the feed line 3F to the return line 3R, the guide member 342 may be provided between the between the feed line 3F and the return line 3R so that the sample rack L is moved from the return line 3R to the feed line 3F, or the guide member 342 may also be provided between the measurement line 3M and the feed line 3F.

Note that although the above embodiment has been described in terms of the sample container T being received into the measuring units 51, 52, 53 at the sample supplying position 35c of the measurement line 3M, the measuring units 51, 52, and 53 also may be configured to directly aspirate the sample from the sample container T being held in the sample rack L on the measurement line 3M.

Although the above embodiment has been described in terms of sample transporting units 3a, 3b, 3c and 4 which are respectively independent of the sample transporting device 3, the present invention is not limited to this configuration. An inseparably integrated sample transporting device may be disposed on the front side of the measuring units 51, 52, 53, and smear sample preparing device 6 so that the sample rack L is transported thereby to each measuring unit 51, 52, 53, and smear sample preparing device 6. In this case, one feed line and one return line are disposed in parallel, and one or a plurality of guide members capable of vertical movement can be disposed between the feed line and the return line.

Although the above embodiment has been described in terms of a sample processing apparatus 1 provided with a blood cell analyzer 5 that classifies and counts blood cells of each type contained in a sample, and a smear sample preparing device 6 for preparing smear samples, the present invention is not limited to this configuration. The sample processing apparatus also may be provided with a clinical sample analyzer other than a blood cell analyzer, such as an immunoanalyzer, blood coagulation measuring apparatus, biochemical analyzer, urine analyzer and the like, so as to transport the blood sample or urine sample to the measuring unit of the clinical sample analyzer.

Although the above embodiment has been described in terms of the blood analyzer 5 being provided with three measuring units 51, 52, 53, and information processing unit 54, the present invention is not limited to this configuration. The measuring units may be provided singly or in plurality, and the measuring unit and information processing unit may be integrated in a single apparatus. The respective measuring units may also be provided with a controller configured by a CPU, memory and the like so that each measuring unit is controlled by its own internal controller and the control of the measuring units 51, 52, 53 is not performed by the information processing unit 54; in this case, the measurement data obtained by the respective measuring units are processed by the information processing unit to generate analysis results of the sample.

What is claimed is:

1. A sample processing apparatus comprising:
   a transporting device configured to transport a sample rack holding a sample; and
   a sample processing device configured to process the sample held by the sample rack transported by the transporting device, wherein
   the transporting device comprises:
   a first transport path configured to transport a sample rack so that the sample rack does not pass through a sample supplying position for supplying the sample to the sample processing device;
   a second transport path configured to transport a sample rack so that the sample rack does not pass through the sample supplying position, the second transport path being disposed parallel to the first transport path;
   a third transport path configured to transport a sample rack so that the sample rack passes through the sample supplying position, wherein the first transport path is arranged between the second transport path and the third transport path;
   a post-analysis rack holder, which is arranged between the first transport path and the third transport path, configured to hold the sample rack transported by the third transport path, the sample rack holding the sample transported to the sample supplying position;
   a rack moving mechanism configured to move the sample rack from the post-analysis rack holder through the first transport path to the second transport path;
   a guide member, which is arranged between the first transport path and the second transport path and movable in vertical directions, configured to allow the sample rack to be moved through the first transport path to the second transport path when the guide member is at a predetermined position, and configured to prevent the sample rack from being moved through the first transport path to the second transport path and prevent a sample rack being transported on the first transport path or the second transport path from deviating from the first or second transport path when the guide member is above the predetermined position; and
   a drive source configured to move the guide member in vertical directions.

2. The sample processing apparatus of claim 1, wherein the guide member comprises a top surface which forms substantially the same plane with the first transport path and the second transport path when the guide member is at the predetermined position.

3. The sample processing apparatus of claim 2, wherein the rack moving mechanism is configured to move the sample rack through the first transport path to the second transport path by sliding the sample rack on the top surface of the guide member when the guide member is at the predetermined position.

4. The sample processing apparatus of claim 1, wherein the guide member comprises a guide part configured to guide the movement of the sample rack through the first transport path to the second transport path when the guide member is at the predetermined position.

5. The sample processing apparatus of claim 1, wherein the guide member comprises a transport stopper configured to stop the sample rack being transported in the first transport path or the second transport path when the guide member is above the predetermined position.

6. The sample processing apparatus of claim 5, wherein the guide member is movable to a first position for preventing the sample rack being transported in the first transport path or the second transport path from deviating from the first or second transport path, and a second position disposed above the first position;
the transport stopper is configured to stop the sample rack when the guide member is disposed at the second position, and not to stop the sample rack when the guide member is at the first position.

7. The sample processing apparatus of claim 1, wherein the transporting device further comprises a preventer wall configured to prevent the sample rack being transported on the second transport path from deviating from the second transport path, wherein the preventer wall is disposed opposite the guide member, with the second transport path interposed therebetween.

8. The sample processing apparatus of claim 1, wherein the third transport path is disposed parallel with the first transport path and the second transport path.

9. The sample processing apparatus of claim 8, wherein the first transport path is a transport path configured to transport the sample rack in the same direction as the transport direction of the third transport path.

10. The sample processing apparatus of claim 8, wherein the second transport path is a transport path configured to transport the sample rack in a predetermined first direction, and the third transport path is a transport path configured to transport the sample rack in a second direction that is a reverse direction of the first direction.

11. The sample processing apparatus of claim 1, further comprising:
a controller configured to control the vertical movement of the guide member by the drive source so that the guide member is at the predetermined position when the sample rack is moving through the first transport path to the second transport path and the sample rack passes the guide member.

12. The sample processing apparatus of claim 11, wherein the controller controls the vertical movement of the guide member by the drive source so that the guide member is above the predetermined position when preventing the sample rack from being moved through the first transport path to the second transport path.

13. The sample processing apparatus of claim 1, wherein the guide member is configured to prevent the sample rack being transported on the first transport path or the second transport path from deviating from the first or second transport path when moved upward from the predetermined position.

14. A sample transporting device comprising:
a first transport path configured to transport a sample rack holding a sample so that the sample rack does not pass through a sample supplying position for supplying the sample to a sample processing device processing the sample held by the sample rack;
a second transport path configured to transport a sample rack so that the sample rack does not pass through the sample supplying position, the second transport path being disposed parallel to the first transport path;
a third transport path configured to transport a sample rack so that the sample rack passes through the sample supplying position, wherein the first transport path is arranged between the second transport path and the third transport path;
a post-analysis rack holder, which is arranged between the first transport path and the third transport path, configured to hold the sample rack transported by the third transport path, the sample rack holding the sample transported to the sample supplying position;
a rack moving mechanism configured to move the sample rack from the post-analysis rack holder through the first transport path to the second transport path;
a guide member, which is arranged between the first transport path and the second transport path and movable in vertical directions, configured to allow the sample rack to be moved through the first transport path to the second transport path when the guide member is at a predetermined position, and configured to prevent the sample rack from being moved through the first transport path to the second transport path and prevent a sample rack being transported on the first transport path or the second transport path from deviating from the first or second transport path when the guide member is above the predetermined position; and
a drive source configured to move the guide member in vertical directions.

15. The sample transporting device of claim 14, wherein the rack moving mechanism is configured to move the sample rack through the first transport path to the second transport path by sliding the sample rack on the top surface of the guide member when the guide member is at the predetermined position.

16. The sample transporting device of claim 14, wherein the guide member comprises a guide part configured to guide the movement of the sample rack through the first transport path to the second transport path when the guide member is at the predetermined position.

17. The sample transporting device of claim 14, wherein the guide member comprises a transport stopper configured to stop the sample rack being transported in the first transport path or the second transport path when the guide member is above the predetermined position.

18. The sample transporting device of claim 17, wherein the guide member is movable to a first position for preventing the sample rack being transported in the first transport path or the sample rack being transported in the second transport path from deviating from the first or second transport path, and a second position disposed above the first position;
the transport stopper is configured to stop the sample rack when the guide member is disposed at the second position, and not to stop the sample rack when the guide member is at the first position.

19. A sample processing apparatus comprising:
a transporting device configured to transport a sample rack holding a sample; and
a sample processing device configured to process a sample held by the sample rack transported by the transporting device, wherein
the transporting device comprises:
a first transport path configured to transport a sample rack so that the sample rack does not pass through a sample supplying position for supplying the sample to the sample processing device;
a second transport path configured to transport a sample rack so that the sample rack does not pass through the sample supplying position, the second transport path being disposed parallel to the first transport path;
a third transport path configured to transport a sample rack so that the sample rack passes through the sample supplying position, wherein the first transport path is arranged between the second transport path and the third transport path;
a post-analysis rack holder, which is arranged between the first transport path and the third transport path, configured to hold the sample rack transported by the third transport path, the sample rack holding the sample transported to the sample supplying position;
a rack moving mechanism configured to move the sample rack from the post-analysis rack holder through the first transport path to the second transport path;
a guide member, which is arranged between the first transport path and the second transport path and movable in vertical directions, configured to prevent the sample rack from being moved through the first transport path to the second transport path and guide a sample rack being transported on the first transport path or the second transport path when the guide member is at a predetermined position;
a drive source configured to move the guide member in vertical directions, wherein
the guide member permits movement of the sample rack through the first transport path to the second transport path by the rack moving mechanism when the guide member is below the predetermined position.

20. A method for transporting a sample rack by a transporting device comprising:
a first transport path configured to transport a sample rack holding a sample so that the sample rack does not pass through a sample supplying position for supplying the sample to a sample processing device configured to process the sample held by the sample rack,
a second transport path configured to transport a sample rack so that the sample rack does not pass through the sample supplying position, the second transport path being disposed parallel to the first transport path,
a third transport path configured to transport a sample rack so that the sample rack passes through the sample supplying position, wherein the first transport path is arranged between the second transport path and the third transport path,
a post-analysis rack holder, which is arranged between the first transport path and the third transport path, configured to hold the sample rack transported by the third transport path, the sample rack holding the sample transported to the sample supplying position, and
a rack moving mechanism configured to move the sample rack from the post-analysis rack holder through the first transport path to the second transport path, comprising the steps of:
moving a guide member which is arranged between the first transport path and the second transport path, to a predetermined position to allow movement of the sample rack through the first transport path to the second transport path when the sample rack is to be moved through the first transport path to the second transport path; and moving the guide member above the predetermined position to prevent the sample rack from being moved through the first transport path to the second transport path and prevent a sample rack from deviating from the first or second transport path when the sample rack is being transport on the first transport path or the second transport path.

* * * * *